(12) United States Patent
Goulko

(10) Patent No.: US 7,799,018 B2
(45) Date of Patent: Sep. 21, 2010

(54) CRYOGENIC APPLICATOR FOR REJUVENATING HUMAN SKIN AND RELATED METHOD

(76) Inventor: Olga Goulko, 2125 Center Ave.-Suite 200, Fort Lee, NJ (US) 07024

( * ) Notice: Subject to any disclaimer, the term of this patent is extended or adjusted under 35 U.S.C. 154(b) by 1168 days.

(21) Appl. No.: 11/432,244

(22) Filed: May 11, 2006

(65) Prior Publication Data

US 2007/0161975 A1 Jul. 12, 2007

Related U.S. Application Data

(60) Provisional application No. 60/757,102, filed on Jan. 6, 2006.

(51) Int. Cl.
*A61B 18/02* (2006.01)
(52) U.S. Cl. .............. 606/20; 606/22; 606/23; 606/26
(58) Field of Classification Search .......... 606/20–26; 607/107, 109
See application file for complete search history.

(56) References Cited

U.S. PATENT DOCUMENTS

| | | | |
|---|---|---|---|
| 3,103,690 A * | 9/1963 | Day ................ 401/147 |
| 3,337,899 A * | 8/1967 | Rentfrow ............ 401/4 |
| 3,869,338 A | 3/1975 | Kavesh |
| 4,032,305 A | 6/1977 | Squires |
| 4,074,717 A | 2/1978 | Schulze et al. |
| 5,330,745 A | 7/1994 | McDow |
| 5,516,505 A | 5/1996 | McDow |
| 5,674,218 A | 10/1997 | Rubinsky et al. |
| 5,738,682 A * | 4/1998 | Jensma ........... 606/23 |
| 5,743,903 A | 4/1998 | Stern et al. |
| 6,106,518 A | 8/2000 | Wittenberger et al. |
| 6,350,276 B1 | 2/2002 | Knowlton |
| 6,413,255 B1 | 7/2002 | Stern |
| 6,551,309 B1 | 4/2003 | LePivert |
| 6,648,904 B2 * | 11/2003 | Altshuler et al. ......... 607/96 |
| 6,726,693 B2 | 4/2004 | Weber et al. |
| 6,749,624 B2 | 6/2004 | Knowlton |
| 6,764,493 B1 | 7/2004 | Weber et al. |
| 6,887,234 B2 | 5/2005 | Abboud et al. |
| 6,905,496 B1 | 6/2005 | Ellman et al. |
| 7,022,121 B2 | 4/2006 | Stern et al. |
| 2005/0043723 A1 | 2/2005 | Howlett et al. |

* cited by examiner

*Primary Examiner*—Linda C Dvorak
*Assistant Examiner*—Jaymi Della
(74) *Attorney, Agent, or Firm*—Charles E. Baxley

(57) ABSTRACT

A cryogenic applicator for rejuvenating skin and a treatment for use of the applicator. A barrel is hand-held. A head is rotatably mounted to the barrel. A cryogenic interface fluidly connects the barrel to a source of a biocompatible non-toxic cryogenic fluid to supply the cryogenic fluid through the barrel to the head that in turn sparges the cryogenic fluid onto the skin quickly, evenly, and smoothly when the head is rolled on the skin, and thereby rejuvenate the skin. The treatment includes the step of rolling the head quickly, smoothly, and evenly over the skin being treated for a period of time in an order of hundredths or tenths of a second, and sparging the cryogenic fluid onto the skin quickly, evenly, and smoothly when the head is rolled on the skin, and thereby rejuvenate the skin.

24 Claims, 6 Drawing Sheets

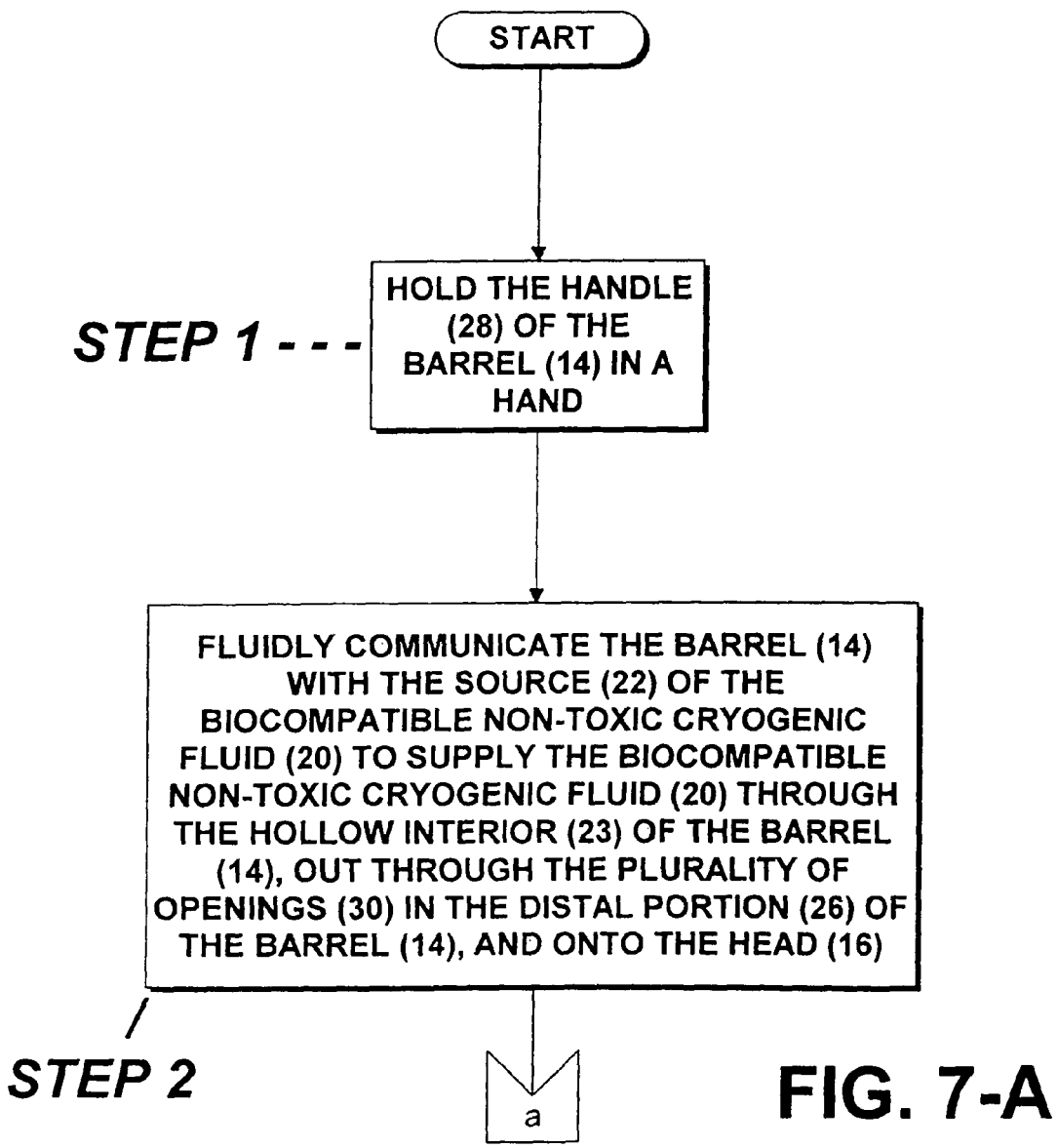
FIG. 7-A

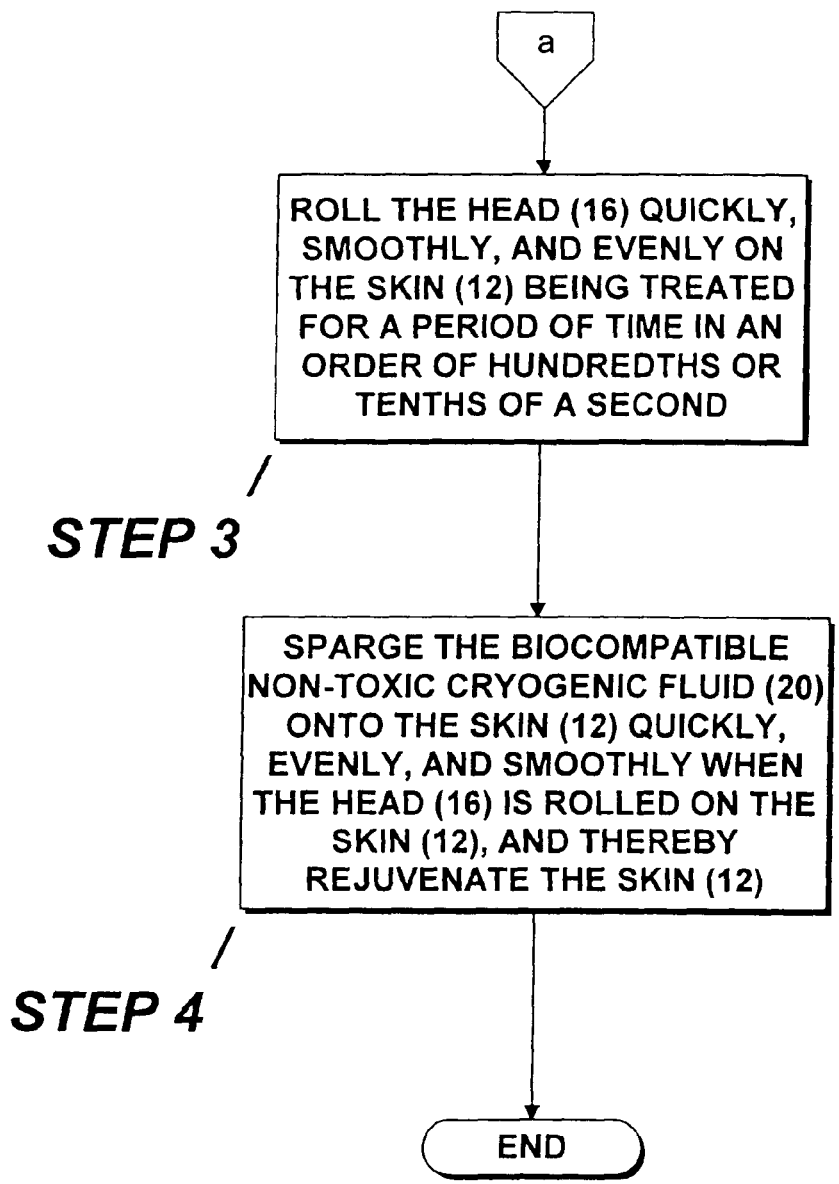
FIG. 7-B

CRYOGENIC APPLICATOR FOR REJUVENATING HUMAN SKIN AND RELATED METHOD

1. CROSS REFERENCE TO RELATED APPLICATIONS

The instant non-provisional patent application claims priority from a parent provisional patent application 60/757,102 filed on Jan. 6, 2006, entitled CRYOGENIC APPLICATOR AND RELATED SKIN TREATMENT.

2. BACKGROUND OF THE INVENTION

A. Field of the Invention

The present invention relates to a cryogenic applicator and, more particularly, to a cryogenic applicator for rejuvenating skin and a method for using the applicator.

B. Description of the Prior Art

Liquid nitrogen, and/or other biocompatible non-toxic cryogenic liquids, all herein sometimes referred to as "cryogenic liquids" is frequently used at offices of physicians in removal of warts, lesions, sun damage and/or the like from a person's skin. For example a method used for removing a wart is to apply liquid nitrogen thereto for a substantial length of time, usually a matter of seconds. The liquid nitrogen has a boiling temperature of approximately −335° F.

Although liquid nitrogen is here mentioned, it will be understood that other suitable biocompatible non-toxic cryogenic liquids could be substituted therefor and the very cold temperature used in the treatment could be different and might vary. In treating the wart, the nitrogen "burns" by freezing the wart.

Numerous innovations for skin rejuvenation have been provided in the prior art that will be described below. Even though each of these innovations may be suitable for a specific purpose to which it is addressed, said innovations all differ in structure and/or technique and/or objective from that of the present invention.

(1) U.S. Pat. No. 4,074,717 to Schulze et al.

U.S. Pat. No. 4,074,717, which issued to Schulze et al. on Feb. 21, 1978, teaches a cryogenic probe, its method of charging, and its method of use. The probe includes a barrel having a plunger mechanism movably mounted therein and a valve on the lower end thereof. The valve normally closes the lower end of the barrel, but the plunger may be moved relative to the barrel to permit cryogenic liquid, such as liquid nitrogen, to by-pass the valve and move upwardly into the interior of the barrel. The valve has a tip portion at the lower end thereof. The barrel is removably positioned in a guard, so that the tip portion extends outwardly through the bottom of the guard whereby the upper end of the plunger is exposed above the guard. The tip portion has a lower end portion which is extremely thin, so that the cryogenic liquid will be positioned closely adjacent the skin, but not in actual contact therewith when the tip portion is placed into contact with the patient's skin.

(2) U.S. Pat. No. 5,330,745 to McDow.

U.S. Pat. No. 5,330,745 issued to McDow on Jul. 19, 1994 and it teaches a method for cryogenically treating a skin lesion employing a hollow fluid retaining device for retaining cryogenic refrigerant in a liquid pool, and then contacting the area of the skin lesion at a temperature and for a time, so that permanent, irreversible rupture of the cellular membrane of the lesion cells occurs.

(3) U.S. Pat. No. 6,350,276 to Knowlton.

U.S. Pat. No. 6,350,276 issued to Knowlton on Feb. 26, 2002 and it teaches a fluid delivery apparatus for introducing a fluid cooling media to a skin surface, including a template with a skin interface surface. An energy delivery device is coupled to the template. A fluid cooling media introduction member is coupled to the template. Resources controllably deliver energy from the energy delivery device to the skin surface. In a related embodiment, the resources are configured to controllably deliver the flowable cooling media to the introduction member. In another embodiment, a sensor is coupled to the resources and to the skin surface.

(4) U.S. Pat. No. 6,726,693 to Weber et al.

U.S. Pat. No. 6,726,693 issued to Weber et al. on Apr. 27, 2004 and it teaches tissue resurfacing accomplished by propelling biocompatible, non-toxic materials at the tissue with sufficient velocity to cause destruction or loosening of tissues to a desired depth. The biocompatible materials are generated by abrading a solid frozen unit and propelling the abraded material onto the surface of the skin or tissue to be treated. A vacuum line near the delivery tip may be used to remove excess materials or reaction by-products building up on the surface of the skin. The treatment system generally includes a control unit, a handheld particle generator, and a cable connecting the control unit to the particle generator. The control unit can include user controls to select particle temperature, particle flux, particle velocity, and vacuum. The handheld particle generator contains a mechanism to push the frozen biocompatible material against a rotating grinding wheel producing the small particles being propelled against tissue being treated.

(5) U.S. Pat. No. 6,749,624 to Knowlton.

U.S. Pat. No. 6,749,624 issued to Knowlton on Jun. 15, 2004 and it teaches a fluid delivery apparatus for introducing a fluid cooling media to a skin surface, including a template with a skin interface surface. An energy delivery device is coupled to the template. A fluid cooling media introduction member is coupled to the template. Resources controllably deliver energy from the energy delivery device to the skin surface. In a related embodiment, the resources are configured to controllably deliver the flowable cooling media to the introduction member. In another embodiment, a sensor is coupled to the resources and to the skin surface.

(6) U.S. Pat. No. 6,764,493 to Weber et al.

U.S. Pat. No. 6,764,493 issued to Weber et al. on Jul. 20, 2004 teaches biocompatible materials being propelled at the skin with sufficient velocity to cause desired resurfacing of tissue to the desired penetration depth. The materials, such as dry ice or water ice, are harmonious with the human body and thus eliminate foreign body reactions. Various materials may be used in combination, including local anesthetics and vasoconstrictors in solid or liquid form. The biocompatible solid or liquid particles are suspended in a cold carrier fluid and are propelled through an insulated delivery system to the surface of the skin. The treatment of diseased skin lesions may be accomplished by its use as a drug delivery system.

It is apparent that numerous innovations for skin treatments have been provided in the prior art. Even though these innovations each may be suitable for a specific purpose to which it is addressed, the innovations would not be suitable, either individually or collectively, for the purposes of the present invention as hereafter described.

3. SUMMARY OF THE INVENTION

A general objective of the present invention is to provide a biocompatible non-toxic cryogenic fluid applicator for rejuvenating skin to overcome disadvantages of the prior art.

Briefly stated, another objective of the present invention is to provide a cryogenic applicator for rejuvenating skin and a treatment using it. A barrel is hand-held. A head is rotatably mounted to the barrel. A cryogenic interface fluidly connects the barrel to a source of a biocompatible non-toxic cryogenic fluid to supply the biocompatible non-toxic cryogenic fluid through the barrel to the head that in turn sparges the biocompatible non-toxic cryogenic fluid onto the skin quickly, evenly, and smoothly when the head is rolled on the skin, and thereby rejuvenate the skin. The treatment includes the steps of holding the barrel in a hand, fluidly communicating the barrel with the source of the biocompatible non-toxic cryogenic fluid to supply the biocompatible non-toxic cryogenic fluid through the barrel, out through multiple openings in the barrel, and onto the head, rolling the head quickly, smoothly, and evenly over the skin being treated for a period of time in an order of hundredths or tenths of a second, and sparging the biocompatible non-toxic cryogenic fluid onto the skin quickly, evenly, and smoothly when the head is rolled on the skin, and thereby rejuvenate the skin.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

4. BRIEF DESCRIPTION OF THE DRAWING

The figures of the drawing are briefly described as follows:

FIGS. 7A-7B is a flowchart sequencing steps in rejeuvenation of the skin utilizing the cryogenic applicator of the present invention.

5. LIST OF REFERENCE NUMERALS UTILIZED IN THE DRAWING

Figure 1:
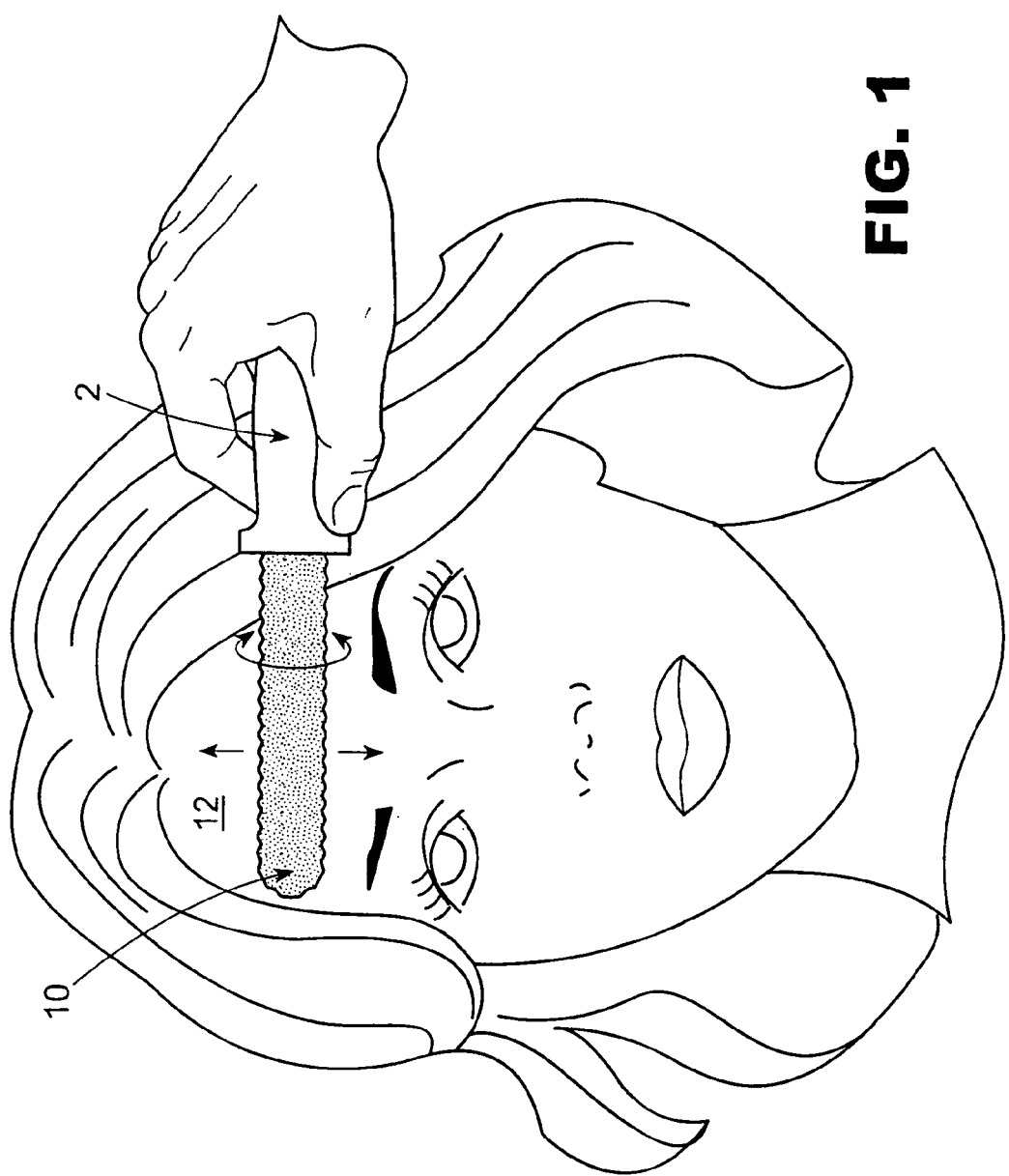
FIG. 1 is a diagrammatic perspective view of the cryogenic applicator according to an embodiment of the present invention for rejuvenating skin on a person's forehead.

10 cryogenic applicator of present invention for rejuvenating skin 12
12 skin
14 barrel
15 flow-control dial
16 head
18 cryogenic interface (such as a supple tube) for fluidly connecting barrel 14 to a source 22 of cryogenic fluid 20 to supply cryogenic fluid 20 through barrel 14 to head 16 that in turn sparges cryogenic fluid 20 onto skin 12 quickly, evenly, and smoothly when head 16 is rolled on skin 12, and thereby rejuvenating skin 12
20 cryogenic fluid
22 source of cryogenic fluid 20
23 interior of barrel 14 for directing biocompatible non-toxic cryogenic liquid 20 to head 16
24 proximal portion of barrel 14
26 distal portion of barrel 14
28 handle of proximal portion 24 of barrel 14 for being hand-held
30 plurality of openings extending radially through and spaced axially along distal portion 26 of barrel 14 and communicating with interior 23 of barrel 14 for passing cryogenic liquid 20 to head 16
32 circumferential groove extending completely around barrel 14
34 end of distal portion 26 of barrel 14
36 tit extending axially outwardly from end 34 of distal portion 26 of barrel 14
38 flexible supply tube of cryogenic interface 18 for fluidly communicating with source 22 of cryogenic fluid 20 to supply cryogenic fluid 20 through interior 23 of barrel 14, out through plurality of openings 30 in distal portion 26 of barrel 14, and onto head 16 that in turn sparges cryogenic fluid 20 onto skin 12 quickly, evenly, and smoothly when head 16 is rolled on skin 12, and thereby rejuvenating skin 12
39 valve for regulating flow of cryogenic fluid
40 drum of head 16
42 web of head 16
44 mesh of drum 40 of head 16
46 soft porous material of web 42 of head 16 for contacting skin 12 in rolling action
48 proximal end of mesh 44 of drum 40 of head 14
50 distal end of mesh 44 of drum 40 of head 14
52 circumferential ring of proximal end 48 of mesh 44 of drum 40 of head 14
54 opening in distal end 50 of mesh 44 of drum 40 of head 14

6. DETAILED DESCRIPTION OF THE PREFERRED EMBODIMENT

A. General.

Referring now to the figures, in which like numerals indicate like parts, and particularly to FIG. 1, which is a diagrammatic perspective view of the cryogenic applicator of the present invention rejuvenating skin (for example) on the forehead, the cryogenic applicator of the present invention is shown generally at 10 for rejuvenating skin 12.

B. Overall Configuration.

The overall configuration of the cryogenic applicator 10 can best be seen in FIG. 2, which an enlarged diagrammatic perspective view of the cryogenic applicator of the present invention identified by ARROW 2 in FIG. 1, and as such, will be discussed in conjunction therewith.

The cryogenic applicator 10 comprises a barrel 14, a head 16, and a cryogenic interface 18. The barrel 14 is hand-held and is provided with a flow-control dial 15. The head 16 is rotatably mounted to the barrel 14. The cryogenic interface 18 is for fluidly connecting the barrel 14 to a source 22 of a biocompatible non-toxic cryogenic fluid 20 to supply the cryogenic fluid 20 through the barrel 14 to the head 16 that in turn sparges the biocompatible non-toxic cryogenic fluid 20 onto the skin 12 quickly, evenly, and smoothly when the head 16 is rolled on the skin 12, and thereby rejuvenating the skin 12. The valve 15 or similar apparatus for controlling flow of the cryogenic liquid can be arranged, as is well known in the art; at the source 22, in the interface 18 or at the barrel 14. The valve 15 or similar apparatus is controllable by the operator by means of the dial 39 using means also well known in the art.

The cryogenic applicator 10 provides a simple, effective means for wrinkle, lesion, and discoloration reduction or elimination thereof from the skin 12. Applicant achieves rejuvenation of the skin 12 by using a quick, smooth, and even application of the cryogenic fluid 20, e.g., liquid nitrogen or other suitable biocompatible non-toxic cryogenic liquid, over one or more substantial surfaced areas of a person's skin 12. Typically the areas of the skin 12 treated include the forehead, the temples, the nose, the cheeks, around the eyes, the cheeks, the chin, the neck, the backs of the hands, and/or other suitable areas for a dramatically shorter time period, typically in the order of hundredths or tenths of a second, so that the cryogenic liquid 20 quickly evaporates, wrinkles, lesions and discolorations are reduced or eliminated, and the skin 12 is rejuvenated. These things happen while the person experiences mild exhilaration. The treatment is painless, eliminating a need for local anesthetic, in fact it is a pleasurable experience. It affects only the epidermal layer(s) of the skin 12 because the cryogenic liquid 20 is applied at its boiling temperature for a very short length of time, so that damage to the epidermal layer does not occur.

With proper operation of the cryogenic applicator 10, heat of the skin 12 very quickly evaporates the cryogenic liquid 20 in at the most one to two seconds to treat wrinkles, blemishes, and/or discolorations without adversely affecting the skin 12. Waste of the biocompatible non-toxic cryogenic liquid 20 is avoided eliminating a need for expensive facilities for storage thereof. The cryogenic applicator 10 is economical to manufacture, reliable, durable, easy and safe to use, refined in appearance, easy to clean, and easy to maintain.

C. Specific Configuration.

Figure 2:
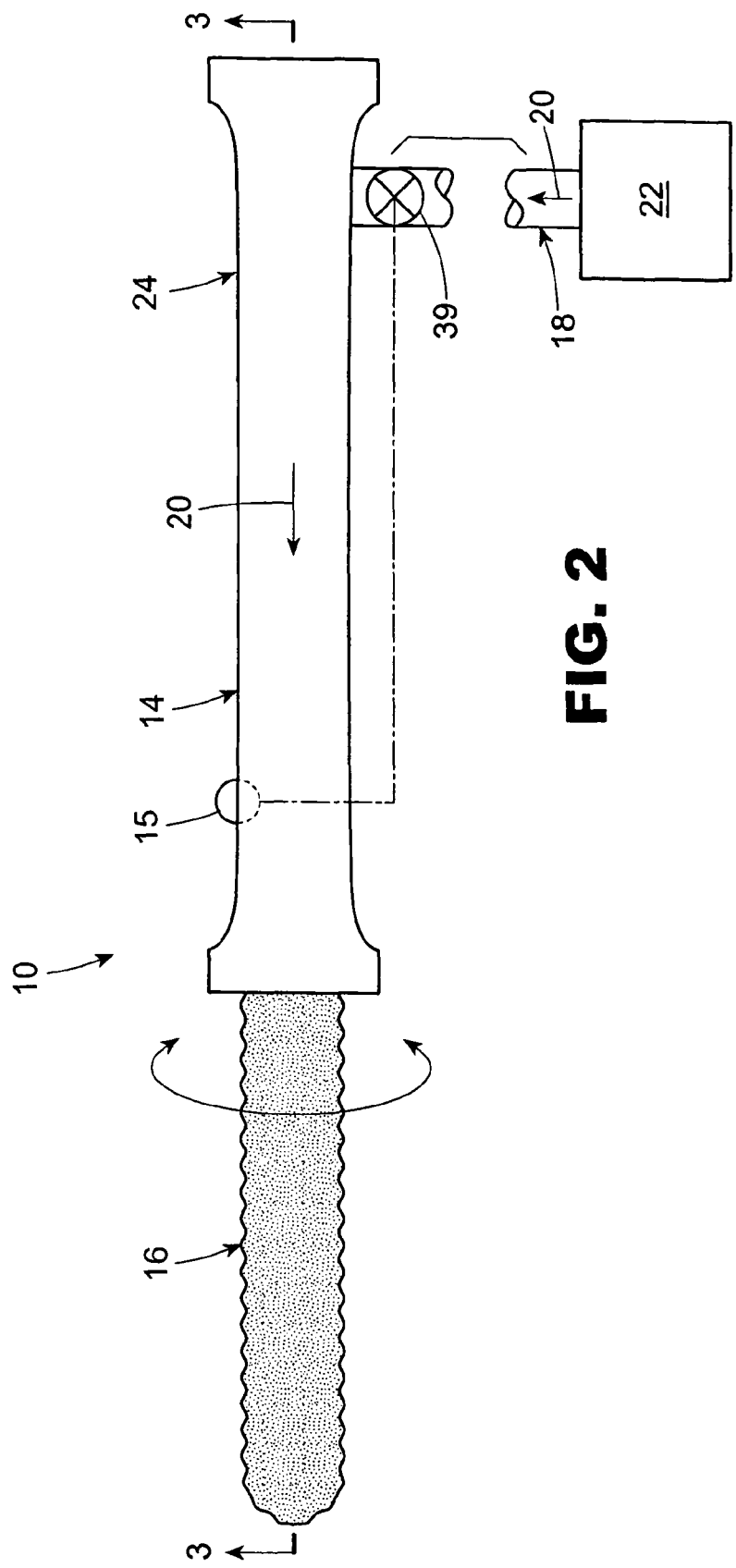
FIG. 2 is an enlarged diagrammatic perspective view of the cryogenic applicator of the present invention identified by ARROW 2 in FIG. 1.
Figure 3:
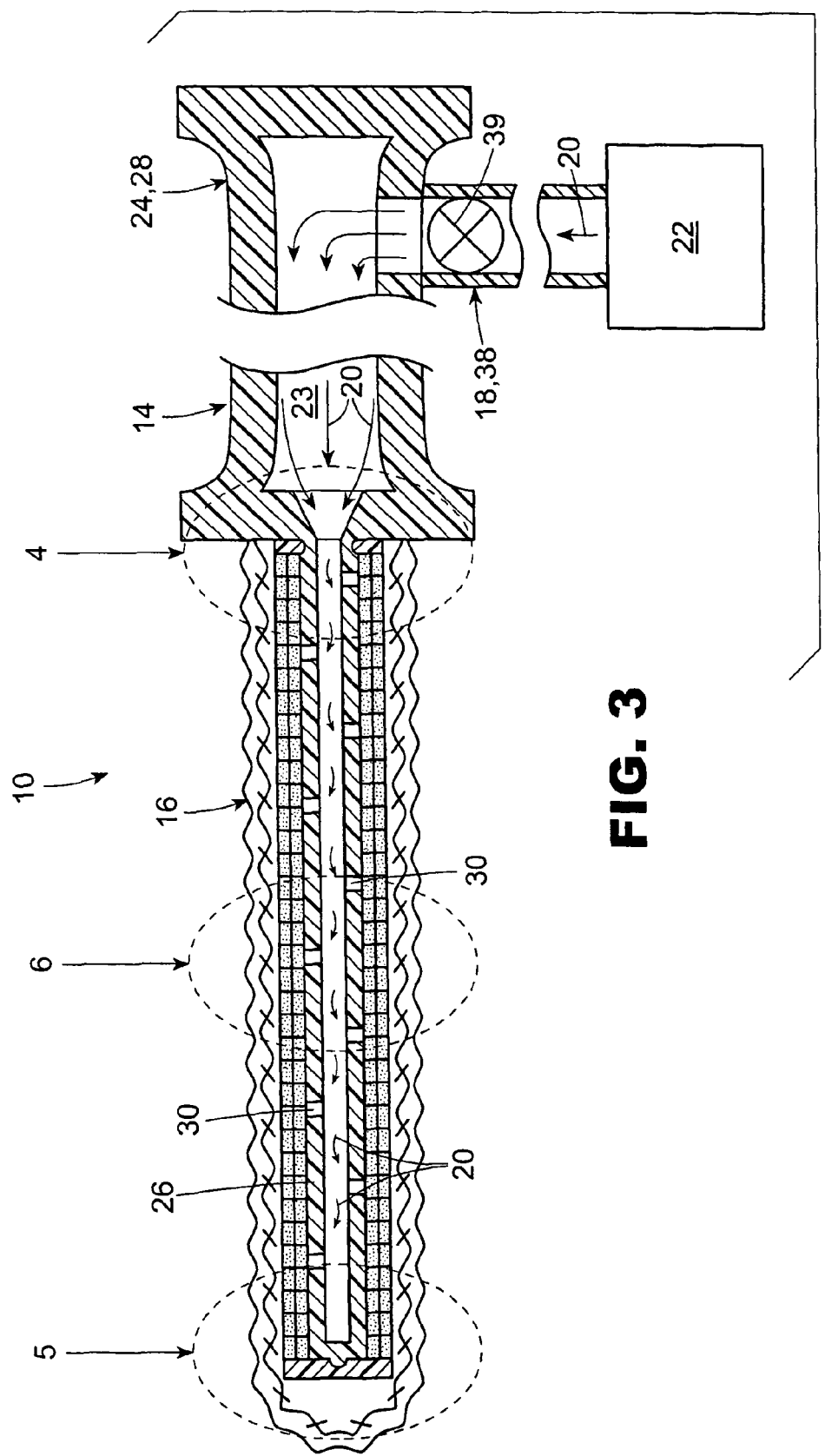
FIG. 3 is an enlarged diagrammatic cross sectional view taken along LINE 3-3 in FIG. 2.

The specific configuration of the barrel 14, the head 16, and the cryogenic interface 18 can best be seen in FIGS. 3-6, which are, respectively, an enlarged diagrammatic cross sectional view taken along LINE 3-3 in FIG. 2, an enlarged diagrammatic cross sectional view of the area generally enclosed by the dotted curve identified by ARROW 4 in FIG. 3, an enlarged diagrammatic cross sectional view of the area generally enclosed by the dotted curve identified by ARROW 5 in FIG. 3, and an enlarged diagrammatic cross sectional view of the area generally enclosed by the dotted curve identified by ARROW 6 in FIG. 3, and as such, will be discussed with reference thereto.

The barrel 14 is slender and elongated and has a hollow interior 23, a proximal portion 24, and a distal portion 26. The hollow interior 23 of the barrel 14 is for directing the biocompatible non-toxic cryogenic liquid 20 to the head 16. The proximal portion 24 of the barrel 14 functions as a handle 28 for being hand-held. The distal portion 26 of the barrel 14 has a plurality of openings 30 extending radially therethrough, spaced axially therealong, and communicating with the hollow interior 23 of the barrel 14 for passing the biocompatible non-toxic cryogenic liquid 20 to the head 16. The source of the cryogenic fluid 20 could be arranged optionally in the barrel 14. By this expedient the interface (supply tube) 18 could be eliminated. The barrel 14 could be thinner and ergonomically shaped, being thinner or wider in its middle. The barrel 14 should heft like a knife handle.

Figure 4:
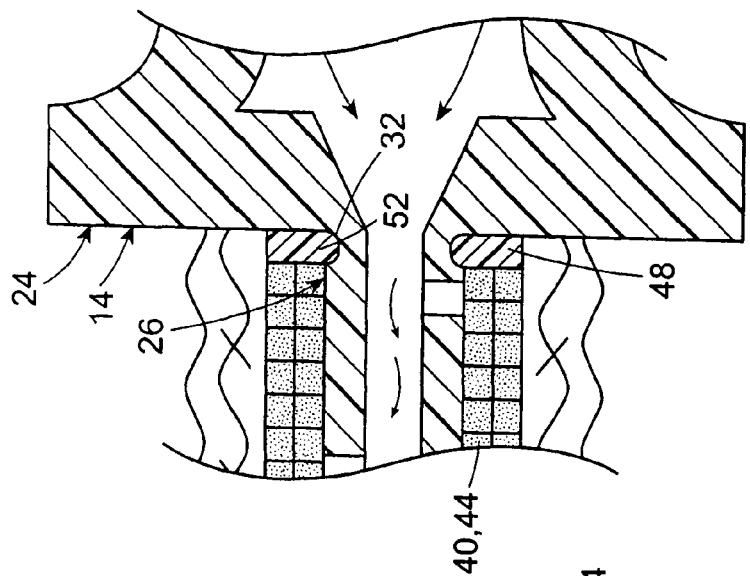
FIG. 4 is an enlarged diagrammatic cross sectional view of the area generally enclosed by the dotted curve identified by ARROW 4 in FIG. 3.

As shown in FIG. 4, the barrel 14 further has a circumferential groove 32 extending completely therearound and being located where the proximal portion 24 of the barrel 14 meets the distal portion 26 of the barrel 14.

Figure 5:
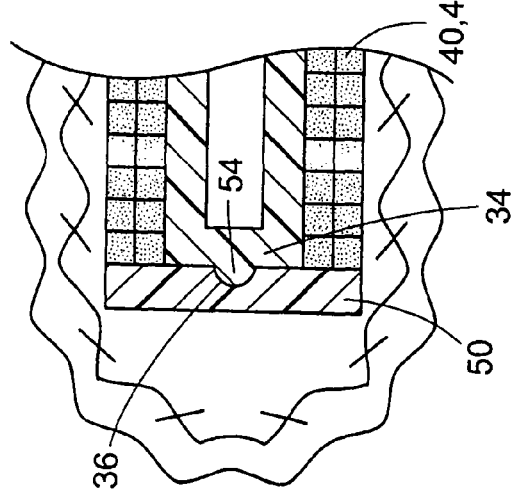
FIG. 5 is an enlarged diagrammatic cross sectional view of the area generally enclosed by the dotted curve identified by ARROW 5 in FIG. 3.

As shown in FIG. 5, the distal portion 26 of the barrel 14 terminates in an end 34. The end 34 of the distal portion 26 of the barrel 14 is closed and has a tit 36 extending axially outwardly therefrom.

Returning now to FIG. 3, the cryogenic interface 18 is a flexible tube 38 fluidly communicating with the proximal portion 24 of the barrel 14 and for fluidly communicating with the source 22 of the cryogenic fluid 20 to supply the cryogenic fluid 20 through the hollow interior 23 of the barrel 14, out through the plurality of openings 30 in the distal portion 26 of the barrel 14, and onto the head 16 (FIG. 6) that in turn sparges the cryogenic fluid 20 onto the skin 12 quickly, evenly, and smoothly when the head 16 is rolled on the skin 12, and thereby rejuvenating the skin 12.

Figure 6:
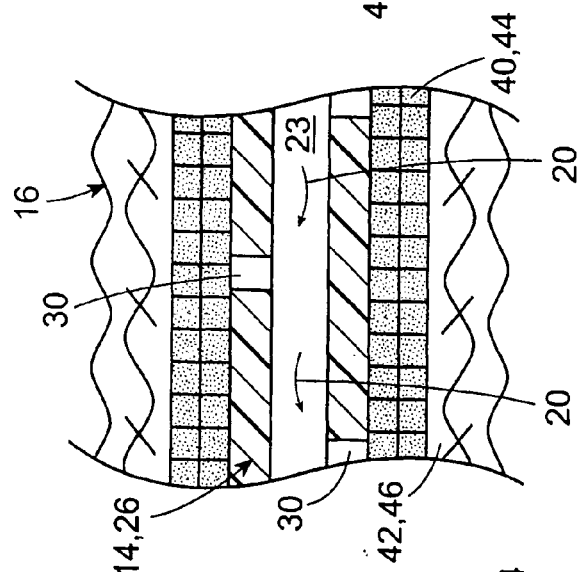
FIG. 6 is an enlarged diagrammatic cross sectional view of the area generally enclosed by the dotted curve identified by ARROW 6 in FIG. 3.

As shown in FIG. 6, the head 16 comprises a drum 40 and a web 42. The drum 40 of the head 16 is open surfaced, such as a mesh 44, and is generally cylindrically-shaped and rotatably mounted to the distal portion 26 of the barrel 14. The web 42 of the head 16 is a soft porous material 46, such as cotton or fabric, woven or non-woven, overlying the mesh 44 of the drum 40 of the head 16 and affixed thereto for contacting the skin 12 in a rolling action. The mesh 44 can be replacably disposable like a sock.

The mesh 44 of the drum 40 of the head 16 provides support for the soft porous material 46 of the web 42 of the head 16, while allowing the cryogenic fluid 20 passing through the plurality of openings 30 in the distal portion 26 of the barrel 14 to pass therethrough and into the soft porous material 46 of the web 42 of the head 16 that in turn sparges the cryogenic fluid 20 onto the skin 12 quickly, evenly, and smoothly when the head 16 is rolled on the skin 12, and thereby rejuvenating the skin 12.

The mesh 44 of the drum 40 of the head 16 has a proximal end 48 (FIG. 4) and a distal end 50 (FIG. 5). As shown in FIG. 4, the proximal end 48 of the mesh 44 of the drum 40 of the head 16 is formed into a circumferential ring 52 rotatably engaging in the circumferential groove 32 in the barrel 14, and as shown in FIG. 5, the distal end 50 of the mesh 44 of the drum 40 of the head 16 has an opening 54 therein rotatably receiving the tit 36 on the end 34 of the distal portion 26 of the barrel 14, for journaling and allowing the head 16 to rotate axially relative to the barrel 14.

It is to be understood that the positioning of the opening 54 and the tit 36 can be reversed without departing from the spirit of the present invention.

D. Treatment.

The treatment for rejuvenating skin 12 utilizing the cryogenic applicator 10 can best be seen FIGS. 7A-7B, which, taken together, are a flowchart sequencing steps for rejuvenating the skin utilizing the cryogenic applicator of the present invention, and as such, will be discussed with reference thereto.

STEP 1: Hold the handle 28 of the barrel 14 in a hand. The dial 15 will be used to control flow of cryogenic fluid 20 using valve 39.

STEP 2: Fluidly communicate the barrel with the source 22 of the cryogenic fluid 20 to supply the cryogenic fluid 20 through the interior 23 of the barrel 14, out through the plurality of openings 30 in the distal portion 26 of the barrel 14, and onto the head 16. Control flow of the cryogenic material (if necessary) by means of the dial 15.

STEP 3: Roll the head 16 quickly, smoothly, and evenly over the skin 12 being treated for a period of time of a different magnitude from typical procedures, such as "burning" of warts, more in the order of hundredths or tenths of a second.

STEP 4: Sparge the biocompatible non-toxic cryogenic fluid 20 onto the skin 12 quickly, evenly, and smoothly when the head 16 is rolled on the skin 12, and thereby rejuvenate the skin 12.

The person experiences a mild tingling and exhilarating feeling. Wrinkles, blemishes, and discolorations are reduced or eliminated. The skin 12 is stimulated and rejuvenated. The old look younger, the young look better, all look happier, their skin 12 looks refreshed, and they feel buoyant. So their usual reaction is to rejoice.

It is to be understood that some other biocompatible non-toxic cryogenic fluid 20 could be used in place of the liquid nitrogen and the form of the handle 28 of the proximal portion 24 of the barrel 14 could be modified. Connection with the supply 22 of the cryogenic fluid 20 and its control 15 and valve 39 could take different forms. Methods of connecting the head 16 mechanically to the barrel 14 for axial rotation thereabout may vary. The materials of the barrel 14 and the head 16 could be either metal, plastic, or some combination thereof, and the cotton of the soft porous material 46 might be replaced typically by a non-woven fabric or any other suitable soft porous material.

E. Conclusions.

It will be understood that each of the elements described above, or two or more together, may also find a useful application in other types of constructions differing from the types described above.

Although the invention has been illustrated and described as embodied in a cryogenic applicator for rejuvenating skin and a treatment using it, however, it is not limited to the details shown, because it will be understood that various omissions, modifications, substitutions, and changes in the forms and details of the device illustrated and its operation can be made by those skilled in the art without departing from the spirit of the present invention.

Without further analysis, the foregoing will so fully reveal the gist of the present invention that others can, by applying current knowledge, readily adapt it for various applications without omitting features that from the standpoint of prior art fairly constitute characteristics of the generic or specific aspects of the invention.

The invention claimed is:

1. A cryogenic applicator for rejuvenating skin, comprising:
    an elongated barrel having a proximal portion and a distal portion, wherein the distal portion is formed with a hollow interior surrounded by a wall, with a plurality of openings radiating from the hollow interior through the wall of the distal portion, and wherein the wall is formed with a circumferential groove located between the proximal portion and the distal portion;
    a head including a cylindrical shaped drum having a proximal end and a distal end, wherein the drum is made of a mesh-like material and wherein the proximal end is formed with a ring engaged with the groove of the barrel for rotation of the drum over the distal portion of the barrel, a web affixed to the drum for rotation therewith, wherein the web is a soft porous material, and further wherein the head is substantially juxtaposed with the distal portion of the barrel; and
    a cryogenic interface; wherein said cryogenic interface supplies a biocompatible non-toxic cryogenic fluid to said head that in turn sparges the biocompatible non-toxic cryogenic fluid onto the skin when said head is rolled on the skin.

2. The applicator of claim 1, wherein the biocompatible non-toxic cryogenic fluid is liquid nitrogen.

3. The applicator of claim 1, wherein said hollow interior of said barrel is for directing the biocompatible non-toxic cryogenic liquid to said head; and wherein said proximal portion of said barrel functions as a handle for being hand-held.

4. The applicator of claim 3, wherein said plurality of openings in said distal portion of said barrel are spaced axially therealong; and wherein said plurality of openings in said distal portion of said barrel communicate with said hollow interior of said barrel for passing the biocompatible non-toxic cryogenic liquid to said head.

5. The applicator of claim 4, wherein said circumferential groove in said barrel extends completely therearound; and wherein said circumferential groove in said barrel is located where said proximal portion of said barrel meets said distal portion of said barrel.

6. The applicator of claim 5, wherein said distal portion of said barrel terminates in an end; wherein said end of said distal portion of said barrel is closed; wherein said end of said distal portion of said barrel has a tit; and wherein said tit on said end of said distal portion of said barrel extends axially outwardly therefrom.

7. The applicator of claim 4, wherein said cryogenic interface is a flexible tube; and wherein said flexible tube of said cryogenic interface fluidly communicates with said proximal portion of said barrel and for fluidly communicating with the source of the biocompatible non-toxic cryogenic fluid to supply the biocompatible non-toxic cryogenic fluid through said hollow interior of said barrel, out through said plurality of openings in said distal portion of said barrel, and onto said head that in turn sparges the biocompatible non-toxic cryogenic fluid onto the skin quickly, evenly, and smoothly when said head is rolled on the skin, and thereby rejuvenating the skin.

8. The applicator of claim 1, wherein said soft porous material of said web of said head is for contacting the skin in a rolling action.

9. The applicator of claim 8, wherein said soft porous material of said web of said head is selected from the group consisting of cotton, fabric, woven, and non-woven.

10. The applicator of claim 8, wherein said mesh of said drum of said head provides support for said soft porous material of said web of said head, while allowing the biocompatible non-toxic cryogenic fluid passing through said plurality of openings in said distal portion of said barrel to pass therethrough and into said soft porous material of said web of said head that in turn sparges the biocompatible non-toxic cryogenic fluid onto the skin quickly, evenly, and smoothly when said head is rolled on the skin, and thereby rejuvenating the skin.

11. The applicator of claim 8, wherein said mesh of said drum of said head has a proximal end; wherein said mesh of said drum of said head has a distal end; wherein said proximal end of said mesh of said drum of said head is formed into a circumferential ring; and wherein said circumferential ring of said proximal end of said mesh of said drum of said head rotatably engages in said circumferential groove in said barrel and said distal end of said mesh of said drum of said head has an opening therein rotatably receiving said tit on said end of said distal portion of said barrel, thereby journaling and allowing said head to rotate axially relative to said barrel.

12. The applicator of claim 8, wherein said barrel is made from a material selected from the group consisting of metal, plastic, and a combination thereof; and wherein said drum of said head is made from a material selected from the group consisting of metal, plastic, and a combination thereof.

13. The applicator of claim 8, wherein said distal portion of said barrel terminates in an end; and wherein said end of said distal portion of said barrel has an opening therein.

14. The applicator of claim 13, wherein said mesh of said drum of said head has a distal end; and wherein said distal end of said mesh of said drum of said head has a tit extending axially inwardly therefrom being rotatably received in an opening in said end of said distal portion of said barrel, thereby journaling and allowing said head to rotate axially relative to said barrel.

15. A cryogenic applicator comprising:
a handle with an elongated barrel having a proximal portion and a distal portion, wherein the distal portion is formed with a hollow interior surrounded by a wall, with a plurality of openings radiating from the hollow interior through the wall of the distal portion, and wherein the wall is formed with a circumferential groove located between the proximal portion and the distal portion;
an applicator head rotatably coupled with said handle, said applicator head including a cylindrical shaped drum having a proximal end and a distal end, wherein the drum is made of a mesh-like material and wherein the proximal end is formed with a ring engaged with the groove of the barrel for rotation of the drum over the distal portion of the barrel, a web affixed to the drum for rotation therewith, wherein the web is a soft porous material, and further wherein the head is substantially juxtaposed with the distal portion of the barrel; and
a cryogenic fluid reservoir in communication with said porous outer surface of said applicator head.

16. The cryogenic applicator of claim 15, further comprising a cryogenic fluid disposed in said cryogenic fluid reservoir.

17. The cryogenic applicator of claim 16, further comprising a valve for regulating flow of said cryogenic fluid to said porous outer surface of said applicator head.

18. The cryogenic applicator of claim 15, further comprising a flexible conduit extending between said cryogenic fluid reservoir and said applicator head for supplying cryogenic fluid to said applicator head.

19. The cryogenic applicator of claim 15, further comprising a barrel projecting from a distal end of said handle, wherein said barrel is integrally formed with said handle and said applicator head is rotatable about said barrel.

20. The cryogenic applicator of claim 15, wherein said porous outer surface of said applicator head comprises a material selected from the group consisting of cotton and fabric.

21. The cryogenic applicator of claim 20, wherein said material selected from the group consisting of cotton and fabric has a tubular shape.

22. The cryogenic applicator of claim 15, wherein said applicator head is elongated and has a substantially cylindrical shape.

23. The cryogenic applicator of claim 19, wherein sand barrel has a hollow interior, an outer wall, and a plurality of openings extending radially through said outer wall.

24. The cryogenic applicator of claim 15, wherein said applicator head comprises:
a cylindrical shaped mesh rotatably mounted to said handle;
a porous material overlying said cylindrical shaped mesh.

* * * * *